(12) United States Patent
Malito et al.

(10) Patent No.: US 8,137,624 B2
(45) Date of Patent: Mar. 20, 2012

(54) METHOD AND APPARATUS FOR ATTACHING A FLUID CELL TO A PLANAR SUBSTRATE

(75) Inventors: Michael P. Malito, Washington, DC (US); Cy R. Tamanaha, Springfield, VA (US); Lloyd J Whitman, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 553 days.

(21) Appl. No.: 11/839,495

(22) Filed: Aug. 15, 2007

(65) Prior Publication Data

US 2008/0044312 A1 Feb. 21, 2008

Related U.S. Application Data

(60) Provisional application No. 60/822,395, filed on Aug. 15, 2006.

(51) Int. Cl.
*G01N 37/00* (2006.01)

(52) U.S. Cl. ....... 422/68.1; 422/500; 422/501; 422/502; 422/503; 422/504; 422/505; 422/506; 422/507; 422/508

(58) Field of Classification Search .............. 422/68.1, 422/100, 500–508
See application file for complete search history.

(56) References Cited

U.S. PATENT DOCUMENTS

| | | | |
|---|---|---|---|
| 3,481,659 A | 12/1969 | Rosenberg | |
| 3,777,283 A | 12/1973 | Elkins | |
| 4,338,024 A | 7/1982 | Botz et al. | |
| 4,505,557 A | 3/1985 | Golias | |
| 4,704,255 A | 11/1987 | Jolley | |
| 5,047,215 A | 9/1991 | Manns | |
| 5,376,252 A | 12/1994 | Ekstrom et al. | |
| 5,443,890 A | 8/1995 | Ohman | |
| 5,486,335 A | 1/1996 | Wilding et al. | |
| 5,640,995 A | 6/1997 | Packard et al. | |
| 5,641,681 A * | 6/1997 | Carter | 436/4 |
| 5,755,942 A | 5/1998 | Zanzucchi et al. | |
| 5,981,297 A | 11/1999 | Baselt | |
| 6,165,739 A | 12/2000 | Clatch | |
| 6,551,841 B1 | 4/2003 | Wilding et al. | |
| 6,857,449 B1 * | 2/2005 | Chow | 137/833 |

(Continued)

OTHER PUBLICATIONS

Becker et al. Polymer microfluidic devices. Talanta 56, 267-287 (2001).

(Continued)

*Primary Examiner* — In Suk Bullock
*Assistant Examiner* — Sharon Pregler
(74) *Attorney, Agent, or Firm* — Amy Ressing; Roy Roberts (57) ABSTRACT

Provided is a method and apparatus for attaching a fluid cell to a planar substrate. The planar substrate may have on it sensors or devices for detecting components within the fluid, and/or be treated to selectively bind or react with components within the fluid. Substrates might include solid-state IC integrated circuit sensor microchips, glass slides, genomic and proteomic arrays, and or other suitable substrates that can make conformal contact with the fluid cell. The fluid cell can be mounted directly on top of the substrate to easily create a fluidic system in a wide variety of implementations. The assembly does not require modification of the substrate; all the fluidic connections are inherent in the apparatus. The present device can be made using low-cost materials and simple methods.

9 Claims, 5 Drawing Sheets

U.S. PATENT DOCUMENTS 7,419,639 B2 * 9/2008 Osterfeld et al. ............ 422/68.1
2004/0253744 A1 12/2004 Rife et al.
2005/0232825 A1 * 10/2005 Fowler et al. ................ 422/121

OTHER PUBLICATIONS

Mastrangelo, et al, Microfabricated devices for genetic diagnostics, Proc. IEEE 86, 1769-1787 (1998).

Bardell, et al., Microfluidic disposables for cellular and chemical detection—CFD model results and fluidic verification experiments. Proc. SPIE 4265, 1-13 (2001).

Hofmann, et al., Three-dimensional microfluidic confinement for efficient sample delivery to biosensor surfaces. Application to immunoassays on planar optical waveguides. Anal. Chem. 74, 5243-5250 (2002).

Li, et al., Biology on a chip: microfabrication for studying the behavior of cultured cells, Crit. Rev. Biomed. Eng. 31, 423-488 (2003).

Erickson, et al., Integrated microfluidic devices. Anal. Chim. Acta 507, 11-26 (2004).

Baselt, et al., A biosensor based on magnetoresistance technology, Biosens, and Bioelectron, 13, 731-739 (1998).

Edelstein, et al., The BARC biosensor applied to the detection of biological warfare agents, Biosens. Bioelectron. 14, 805 (2000).

Miller, et al., A DNA array sensor utilizing magnetic microbeads and magnetoelectronic detection, J. Mag. Mag. Mat. 225, 138 (2001).

Tamanaha. et al, Magnetic method for DNA detection on an arrayed solid state device, Micro Total Analysis Systems 2001, (Kluwer Academic Publishers, Boston, pp. 444-446) (2001).

Whitman, et al., The BARC biosensor, 2001 NRL Review, p. 99.

Rife, et al., Design and performance of GMR sensors for the detection of magnetic microbeads in biosensors, Sensors and Actuators A 107, 209-218 (2003).

Sheehan, et al., Detection limits for nanoscale biosensors, Nano Lett. 5, 803-807 (2005).

Malito, et al., A simple Multichannel Fluidic System for Laminar Flow over Planar Substrates, NRL/MR/6170-06-8953 (NRL Memorandum Report) (Apr. 21, 2006).

* cited by examiner

METHOD AND APPARATUS FOR ATTACHING A FLUID CELL TO A PLANAR SUBSTRATE

CROSS-REFERENCE TO RELATED APPLICATIONS

This Application is a Non-Prov of Prov (35 USC 119(e)) application 60/822,395 filed on Aug. 15, 2006, incorporated herein in its entirety by reference.

BACKGROUND OF THE INVENTION

There are numerous uses for applying a fluid to a planar substrate. For example, the substrate may have on it sensors or devices for detecting components within the fluid, and/or be treated to selectively bind or react with components within the fluid. Substrates might include solid-state IC sensor chips, glass slides, genomic and proteomic arrays, and or other reagents chemically attached or dried onto the substrate. One challenge to such applications is reliably and easily attaching some type of fluid chamber or flow cell to the substrate.

One use where the methods and apparatus for applying a fluid to a planar substrate is applicable is in "lab-on-a chip" (or LOC) devices. LOC devices use microliter-scale volumes and millimeter-to-micrometer-scale components to replace bench-top chemical and biochemical instrumentation. Several benefits of such devices over standard laboratory systems include reduced consumption of reagents, reduced volume of waste products, easier controlled process parameters, increased reaction time, and more rapid chemical analysis.

One hallmark of LOC systems is the ability to perform a number of individual tests in parallel on a planar surface. For example, a typical planar DNA oligonucleotide microarray may consist of 50 to 200 micrometer-diameter spots deposited with a robotic spotter onto the substrate in a grid pattern. The array can include up to several thousand (cf. 30,000) unique DNA probe sequences and is, operationally, at least several thousands of experiments running in parallel.

A key component of any assay incorporating a biochemical capture surface such as these is the method by which sample containing the target, along with any other required reagents, are delivered to the capture surface. Most often the reagents are delivered in a static fluidic environment, such as a microtiter well. More recently, a variety of microsystems have been developed to deliver the fluid under dynamic (often laminar) flow over planar substrates. For example, see Becker et al. Polymer microfluidic devices. Talanta 56, 267-287 (2001), Mastrangelo, et al, Microfabricated devices for genetic diagnostics, Proc. IEEE 86, 1769-1787 (1998). Bardell, et al., Microfluidic disposables for cellular and chemical detection—CFD model results and fluidic verification experiments. Proc. SPIE 4265, 1-13 (2001), Hofmann, et al., Three-dimensional microfluidic confinement for efficient sample delivery to biosensor surfaces. Application to immunoassays on planar optical waveguides. Anal. Chem. 74, 5243-5250 (2002), Li, et al., Biology on a chip: microfabrication for studying the behavior of cultured cells, Crit. Rev. Biomed. Eng. 31, 423-488 (2003), and Erickson, et al., Integrated microfluidic devices. Anal. Chim. Acta 507, 11-26 (2004). The challenge becomes how to integrate the fluidics along with the chosen detection technology (i.e. electrical, optical, etc.) with these substrates on this small size scale.

Examples of fluidic devices designed to handle multiple samples or assay protocols include inventions by H. J. Rosenberg, U.S. Pat. No. 3,481,659 include Elkins, U.S. Pat. No. 3,777,283, G. Bolz et al., U.S. Pat. No. 4,338,024, Golias, U.S. Pat. No. 4,505,557. Clatch, U.S. Pat. No. 6,165,739, and Wilding, et al., U.S. Pat. No. 6,551,841.

There are also a number of commercially available slides incorporating multiple fluidic compartments or the means to create individual chambers on the slide (e.g., Fisher Scientific, Grace Bio-Labs). Various custom microliter volume flow cells made of quartz or molded from polydimethylsiloxane (PDMS), as well as a multi-well, flow-through hybridization chamber which incubate three whole chips in parallel for magnetic force discrimination assays have been disclosed. See Malito et al., A Simple Multichannel Fluidic System for Laminar Flow Over Planar Substrates. NRL/MR/6170-06-8953; MR-8953, (2006).

In general, the approaches taken by these devices are guided by the applications addressed. For example, devices may isolate separate volumes on a single microscope slide in order to analyze several samples at once (in static volumes). Other devices contain a single channel for the purpose of analyzing individual particles. In general, however, none of these devices, with the exception of the devices disclosed by Clatch, Wilding, Covington and Malito, are appropriate for conducting assays under controlled flow rates. Although the devices by Clatch and Wilding could be used for monitoring different reactions or assay conditions in parallel, the devices as reported require complex semiconductor microfabrication methods, are designed to share reagents from a single reservoir, or the reagents are distributed by uncontrolled capillary action. Covington's device requires several layers of stencil material to form multichannels, and no clear means to connect their devices to fluidic sources is indicated.

Methods and devices currently in use are encumbered by complicated designs and manufacturing methods making them unsuitable for mass production, to be used as a cheap disposable end-product, or to be compatible with standard off-the-shelf pumping and valving components. See, for example, Jolley, U.S. Pat. No. 4,704,255, Manns, U.S. Pat. No. 5,047,215, Shartle, U.S. Pat. No. 5,627,041, Packard et al., U.S. Pat. No. 5,640,995, and Zanzucchi, et al., U.S. Pat. No. 5,755,942.

Another deficiency of most microfluidic systems is that their complicated construction and usage are not conducive for handling as a simple tool that can be routinely assembled and reused by a laboratory technician with the same ease of, say, a standard micropipettor. Brevig et al., Hydrodynamic guiding for addressing subsets of immobilized cells and molecules in microfluidic systems. BMC Biotechnology 2003, 3:10 (Sep. 19, 2005) discloses a simple docking station that provides a mechanical force for sealing a flat substrate (e.g. glass slide) against a single microfluidic cell without any adhesives or bonding strategies. The flow cell was also designed to actively direct the trajectory and control the width of the sample stream using two additional guiding streams. However, manipulating the individual flow rates of the guiding streams adds a layer of complexity to the external fluidic control requirements. Another deficiency is that the dock is only capable of operating a single fluid cell, and hence a single assay.

The assembly of the different layers of the fluidic device, in particular the cover plate that encloses the channels, have relied on mechanisms such as adhesives, thermal bonding under high compression, chemical bonding, hot gas welding, and ultrasonic welding. Of these, adhesives are the dominant means for assembly.

Covington et al., U.S. Pat. No. 6,848,462 discloses an adhesiveless microfluidic device having several microchannel formats dictated by what they describe as stencil layers which can easily be changed to rapid prototype different channel geometries. However, construction of their device could require compressing several stencil layers between at least two thermoplastic cover layers under high pressure and temperature. Alignment pins are required by other incarnations of their device to properly orient the various layers of material.

Ekström et al., U.S. Pat. No. 5,376,252 and Öhman, U.S. Pat. No. 5,443,890 make use of an elastomer spacing layer or injected sealing material that forms a sealed microchannel between at least two cover plates under moderate pressure. In both disclosures, grooves and/or ridges must first be made into the cover plates to stabilize the material. A deficiency with this design is the channel geometry must be permanently defined in the substrates. If a new channel geometry is required, new substrates must be made.

BRIEF SUMMARY OF THE INVENTION

Provided is a fluidic cell comprising a support body having a receiving surface for a substrate, a recessed area having a depth located within said receiving surface, a mesa located within said recessed area, wherein said mesa has a height that is less than the depth of the recessed area. The mesa has at least two fluidic ports. A substrate is connected to the receiving surface with a compressible layer between the support body and substrate. The compressible layer is located around the mesa and defines the side walls of the fluidic cell. The compressible layer also provides a seal around the mesa when said support body and said substrate are connected. The difference between said depth of said recessed area and said height of said mesa is the height of said fluidic cell. The support body may also have a raised ledge located around the compressible layer. Typically, the compressible layer is comprised of an elastomer material. Additionally, the support body further comprises a raised ledge or other raised features that are used to align the substrate on the support body. Typically, the substrate is a carrier board having a sensor chip, wherein said carrier board is in connection with said support body.

DETAILED DESCRIPTION OF THE INVENTION

The method and apparatus for attaching a fluid cell to a planar substrate provided responds to the need for the quick assembly of assay cartridges for a magnetic label-based biosensor called the compact Bead Array Sensor System (cBASS®). This biosensor system uses Bead ARray Counter (BARC®) and related technologies for multiplexed detection of proteins, bacteria, and viruses, including nucleic acids and toxins. In that biosensor, magnetic microbeads are used to label biomolecules captured onto a receptor-patterned microchip that contains an embedded array of magnetic microsensors. See Baselt, U.S. Pat. No. 5,981,297; Baselt, et al., A biosensor based on magnetoresistance technology, Biosens, and Bioelectron, 13, 731-739 (1998); Edelstein, et al., The BARC biosensor applied to the detection of biological warfare agents, Biosens. Bioelectron. 14, 805 (2000); Miller, et al., A DNA array sensor utilizing magnetic microbeads and magnetoelectronic detection, J. Mag. Mag. Mat. 225, 138 (2001); Tamanaha. et al, Magnetic method for DNA detection on an arrayed solid state device, Micro Total Analysis Systems 2001, (Kluwer Academic Publishers, Boston, pp. 444-446) (2001); Whitman, et al., The BARC biosensor, 2001 NRL Review, p. 99; and Rife, et al., Design and performance of GMR sensors for the detection of magnetic microbeads in biosensors, Sensors and Actuators A 107, 209-218 (2003).

The sensors in the BARC microchip are micron-scale wire-like structures made with giant magnetoresistive (GMR) material. When a magnetic bead is present above a GMR sensor, the resistance decreases by a detectable amount; the more beads present, the larger the decrease. The assay on the BARC chip requires an integrated fluid cell and laminar flow conditions. In addition to improving the capture and labeling of any targets in the sample, the laminar flow can be adjusted to apply controlled fluidic forces to the microbeads on the chip surface in order to selectively remove those that are not specifically labeling captured target molecules, see Sheehan, et al., Detection limits for nanoscale biosensors, Nano Lett. 5, 803-807 (2005) and Rife, et al., US Patent Publication 20040253744. This unique assay step, called fluidic force discrimination (FFD), greatly reduces unwanted background signal, enabling the rapid identification of captured biomolecules with high sensitivity and specificity with little or no sample processing. Highly sensitive multiplexed DNA assays (<10 fM) and immunoassays (<10 pg/mL) have been demonstrated in less than 20 minutes, without amplification or pre-concentration steps, using a variety of complex sample matrices such as blood and food products.

Although the use of magnetic labels and chip-based magnetoelectronic detection provides many advantages of the cBASS™, the assay performance is independent of the magnetoelectronics which counts the beads, and can be optimized separately from the magnetoelectronics. The system performance is currently determined by the assay, which ultimately determines how many beads are available for detection, and the bead label density can alternately be determined using optical microscopy and particle counting. Therefore, it is desirable to develop assays using a method and apparatus for attaching a fluid cell to a planar assay substrate that can be used either with a BARC™ sensor chip or a simpler substrate with similar chemistry. In this way, assays can be developed without having to consume BARC™ prototype microchips. In addition, the ability to perform multiple assays in parallel in different flow cells with a single substrate would enhance the ability to optimize assay protocols.

What would be desirable, therefore, is a simple, reusable fluid cell with a "press-together" design that is flexible enough to be integrated into a range of devices from disposable assay cartridges to experimental multi-channel assay platforms. Control of channel headspace for obtaining optimum mass transfer conditions, and channel geometry for fluid control based on a given sensor layout should be easy to rapidly prototype without affecting the substrate on which the assay is being performed. The integrated fluid cell should also be able to function without affecting other components attached to the substrate such as wire bonds used for establishing electronic connections to embedded sensors. The design should also be able to accommodate heterogeneous assays on a solid substrate using laminar flow and optical inspection.

The basic "press-together" assembly consists of three standard components: 1) a support body, typically plastic, in which the integrated fluid cell mesa is machined into; 2) an elastomer gasket which functions as the side walls of the integrated fluid cell and establishes a water tight seal against the support body and the planar substrate: and 3) a planar substrate which may be a sensor chip, glass slide. etc. A key feature of this invention is that the fluid cell design is independent of the support body. The cell design is restricted only by the surface area and location of the assay reaction on the planar substrate on which the fluid cell contacts. In the case of an IC microchip, other considerations may include the presence of wire bonds to the edge of the chip that the mesa must be designed to avoid. Therefore the basic design and manufacturing process is identical whether it is for a cartridge or a multi-channel platform for microscope observation. Another feature is that embodiments which use compression of a silicone (or similar elastomer) layer to form the water-tight seal are completely reusable after disassembling. The assembly is configured for repeated non-destructive separation and reassembly.

Figure 1A:
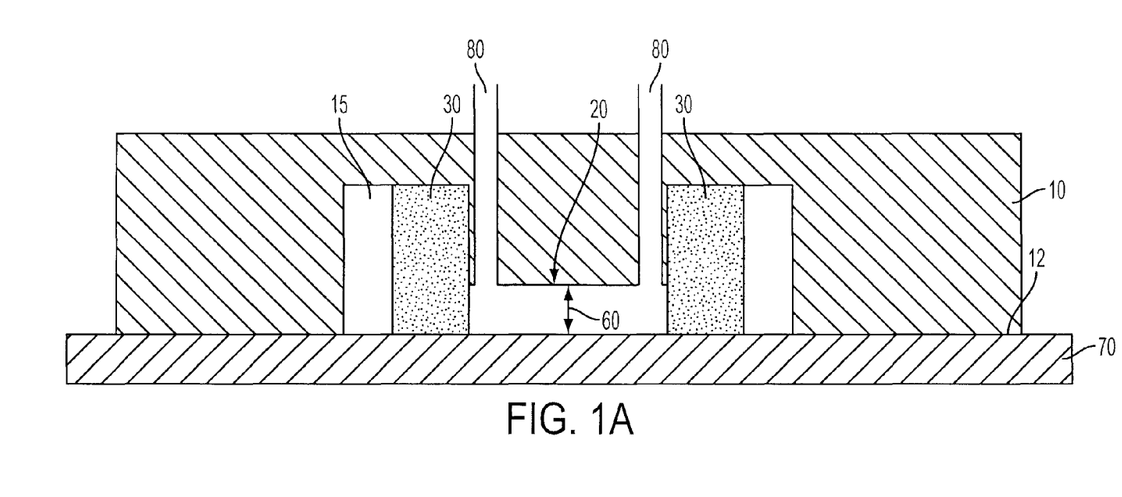
FIG. 1 is an embodiment of the fluidic cell.
Figure 1B:
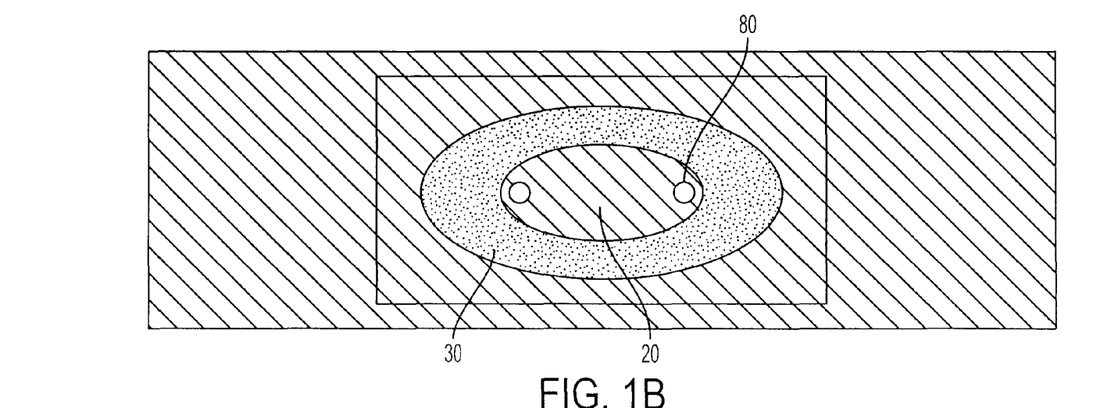

The general process begins with the design of the cell geometry using a CAD program such as AutoDesk Inventor®. Code is generated for programming a CNC milling machine to automatically mill a free-standing mesa into the plastic support body which forms the foundation for the integrated fluid cell. FIG. 1a is a side view of the fluidic cell. FIG. 1b is a top view of the fluidic cell. FIG. 1 shows the support body 10 having a receiving surface 12, for receiving a substrate, 70. The support body 10 has a mesa 20 located in a recessed area 15. The basic integrated fluid cell structure has a silicone (or similar elastomer) compressible layer (i.e. gasket) 30 around the mesa 20. The depth of the recessed area 15 less the height of the mesa is the height 60 of the interior volume of the fluidic cell once the plastic support body 10 and planar substrate 70 are secured together. This height is carefully measured to achieve the appropriate fluidic cell height to optimize fluid flow versus mass transfer conditions for the intended biochemical assay application. Fluidic inlet and outlet ports 80 are drilled in the mesa 20 for the attachment of external tubing or merging to extended channels milled into the support body 10. Optionally, a recessed ledge frame (not shown) of appropriate depth is machined into the support body 10 where the planar substrate 70 will be seated in order to assist with alignment of the components. Typically, a mold is constructed in which silicone gaskets can be cast in the shape of the integrated cell. A gasket mold was made from an aluminum block. A gasket (e.g., silicone elastomer) was cast from the mold. Once cast, the silicone gasket 30 is placed around the mesa 20. To complete the assembly, a planar substrate 70 is press-fit or secured permanently with screws into the support body 10. The substrate 70 makes contact with the silicone gasket 30 and enough pressure is applied to form a water-tight seal around the mesa 20. Typically, the height of the flow cell ranges from about 10 micrometers to about 1000 micrometers. More preferably, the height of the flow cell is about 100 micrometers. The compressible material acts to seal the fluidic cell and acts as a side wall to the fluidic cell. For structural integrity and ensuring a water-tight seal when the substrate and support body are compressed together, the free-standing gasket 30 has thicker walls defined by the surface area limits of the planar substrate and is molded to fit snugly around the mesa 20.

Figure 2A:
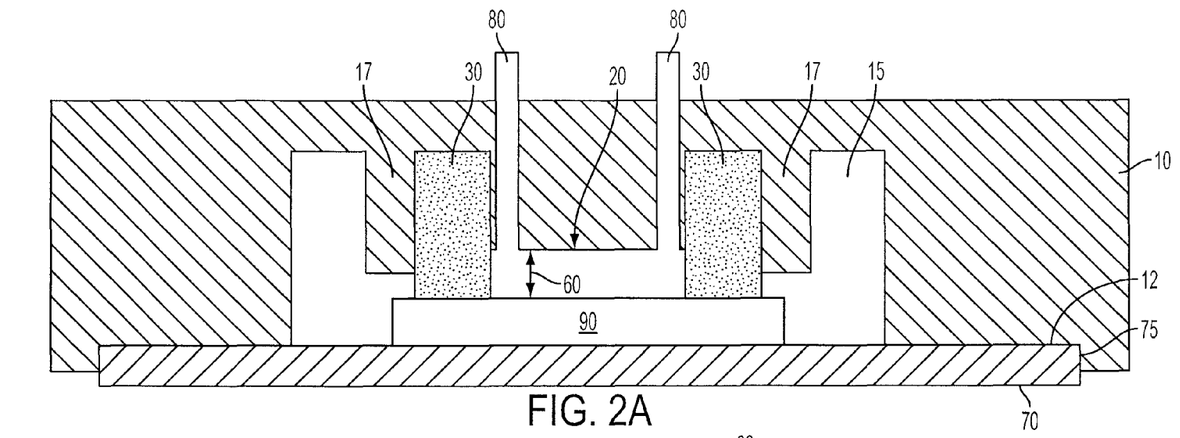
FIG. 2 a an embodiment of the fluidic cell.
Figure 2B:
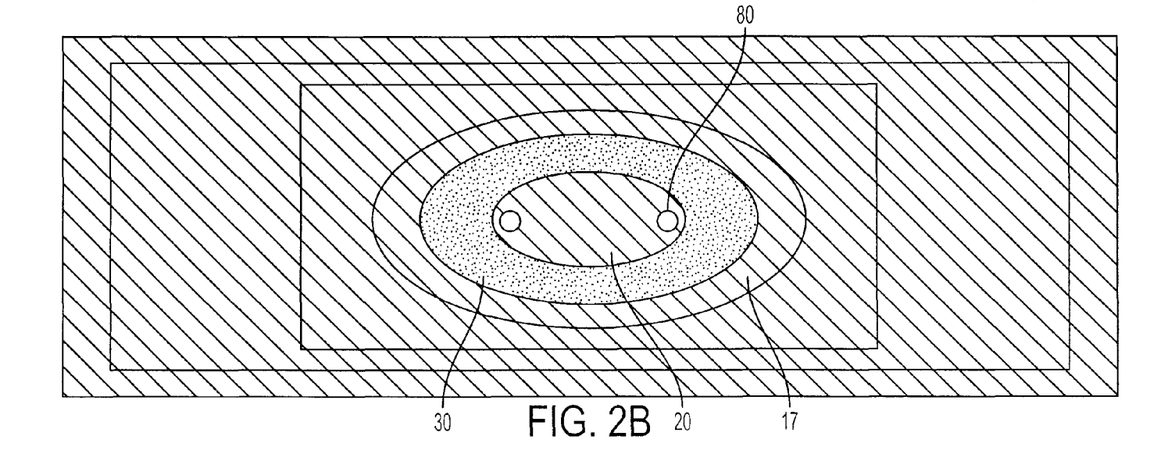

FIG. 2a is a side view of a second embodiment of the fluidic cell. FIG. 2b is a top view of the fluidic cell. FIGS. 2a and 2b depict a flow cell as in FIG. 1, however, the support body 10, further comprises a raised ledge 17 located around the gasket 30, effectively creating a groove in the support body 10 that receives the gasket 30. A recessed ledge frame 75 of appropriate depth is machined into the support body 10 where the planar substrate 70 will be seated in order to assist with alignment of the components. While under compression, the gasket 30 expands and is stabilized within this raised ledge 17, allowing for firm seating of the gasket 30 around the mesa 20. This embodiment does not need thicker walls because the raised ledge assists in maintaining structural integrity and ensuring a water-tight seal. FIG. 2 further depicts a chip, 90, on top of the substrate 70.

Figure 3A:
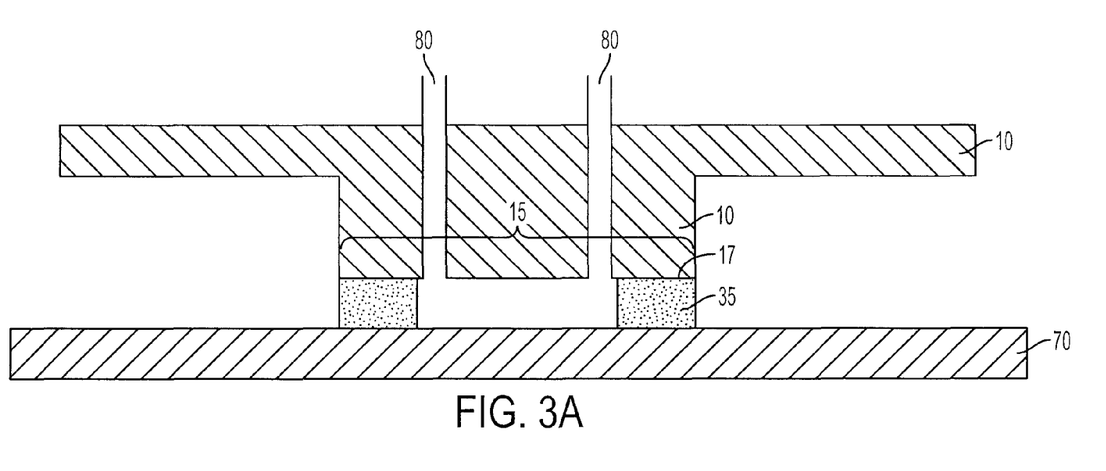
FIG. 3 an embodiment of the fluidic cell.
Figure 3B:
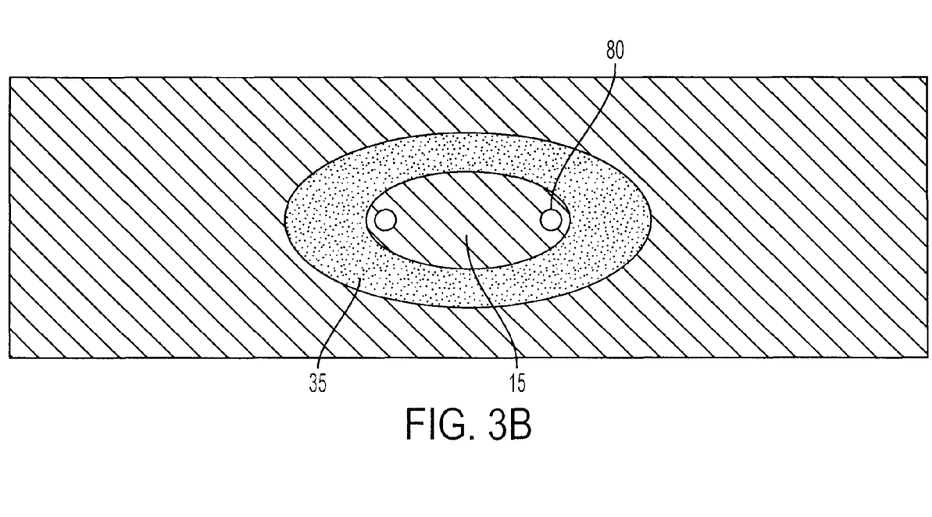

As depicted in FIGS. 3a (side view), and 3b (top view), instead of a silicone elastomer gasket for sealing, an adhesive layer 35 (such as double-sided acrylic tape) is used in the third embodiment. This method is meant for a permanent assembly of the integrated flow cell—the substrate 70 will not be reusable and is meant to be part of a disposable device. This embodiment of the fluidic cell comprises a support body 10 having a receiving surface 17 for a substrate 70, a recessed area 15 having a depth located within said support body, and at least two fluidic ports 80 located within said recessed area 15. An adhesive layer 35 is located on the receiving surface 17. The adhesive layer 35 has a known thickness. A substrate 70 is in connection with the adhesive layer 35. The adhesive layer 35 provides a seal around the recessed area 15 when said support body 10 and said substrate 70 are connected. The depth of the recessed area plus the thickness of the adhesive layer defines the height of the fluidic cell.

Figure 4A:
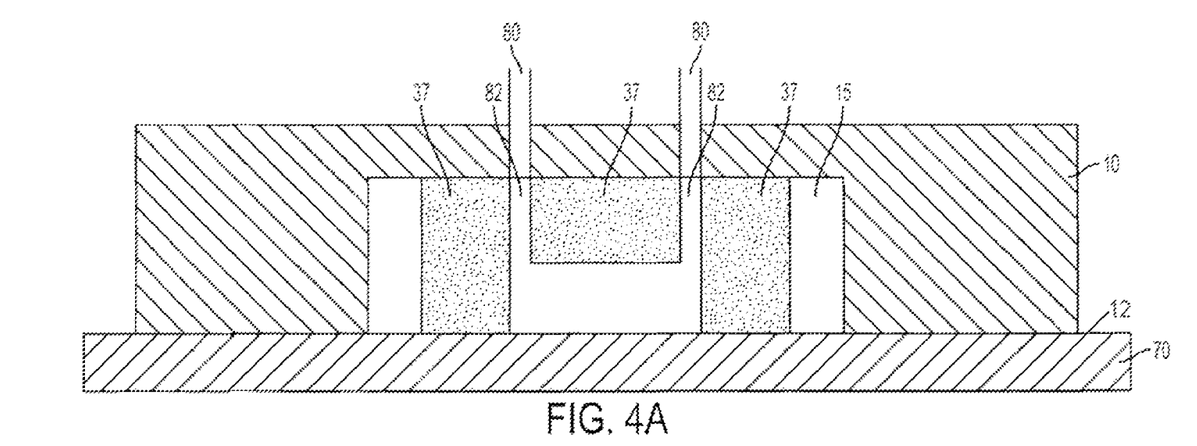
FIG. 4 an embodiment of the fluidic cell.
Figure 4B:
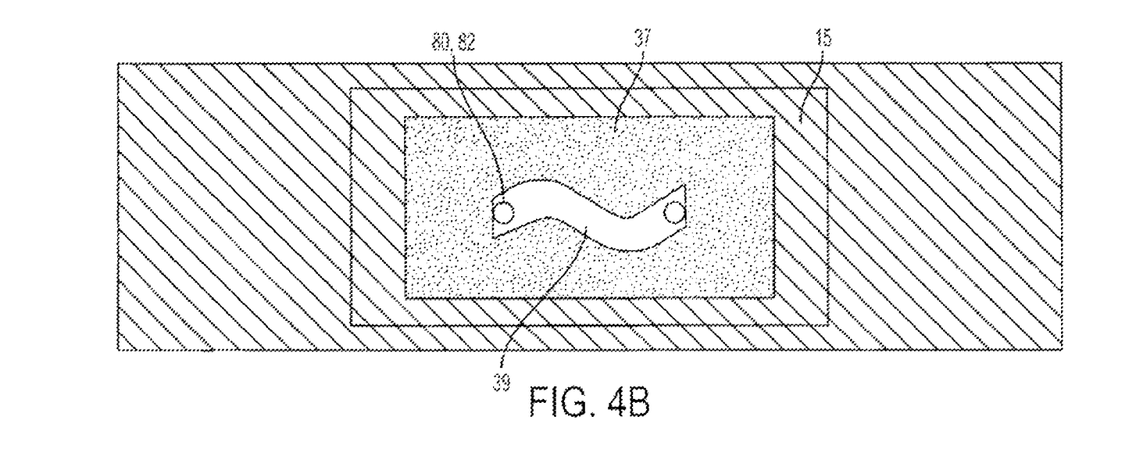

As depicted in FIG. 4 (side view) and 4b (top view) the fourth embodiment, unlike the first other embodiments, the gasket 30 alone defines the fluidic cell. The support body 10 has a receiving surface 12 for a substrate 70. A recessed area 15 having a depth is located within the receiving surface 12. At least two fluidic ports 80 are located within the recessed area 15. A compressible sheet 37 (typically an elastomer material) having a height greater than the depth of said recessed area 15 is located within the recessed area. The compressible sheet 37 has at least two fluidic ports 82, that are aligned with the fluidic ports of the recessed area 15 of the support body 10. The compressible sheet 37 has open channel 39 located between the fluidic ports 82. The open channel 39 is located on the surface of the compressible sheet 37 facing the substrate 70. The open channel 39 has a depth. When the substrate 70 is connected to the support body 10 receiving surface 12, the compressible sheet 37 is compressed. The depth of the open channel 39 after the compressible sheet 37 is compressed is the height of said fluidic cell. One advantage to this embodiment is that different compressible sheets having different flow cell heights and geometries can be placed in the recessed area of the support body, for example serpentine channels can be designed in positive relief. Those familiar in the art will see the versatility in rapidly switching from one flow cell design to another by simply changing compressible sheet inserts into a recessed area.

Figure 5:
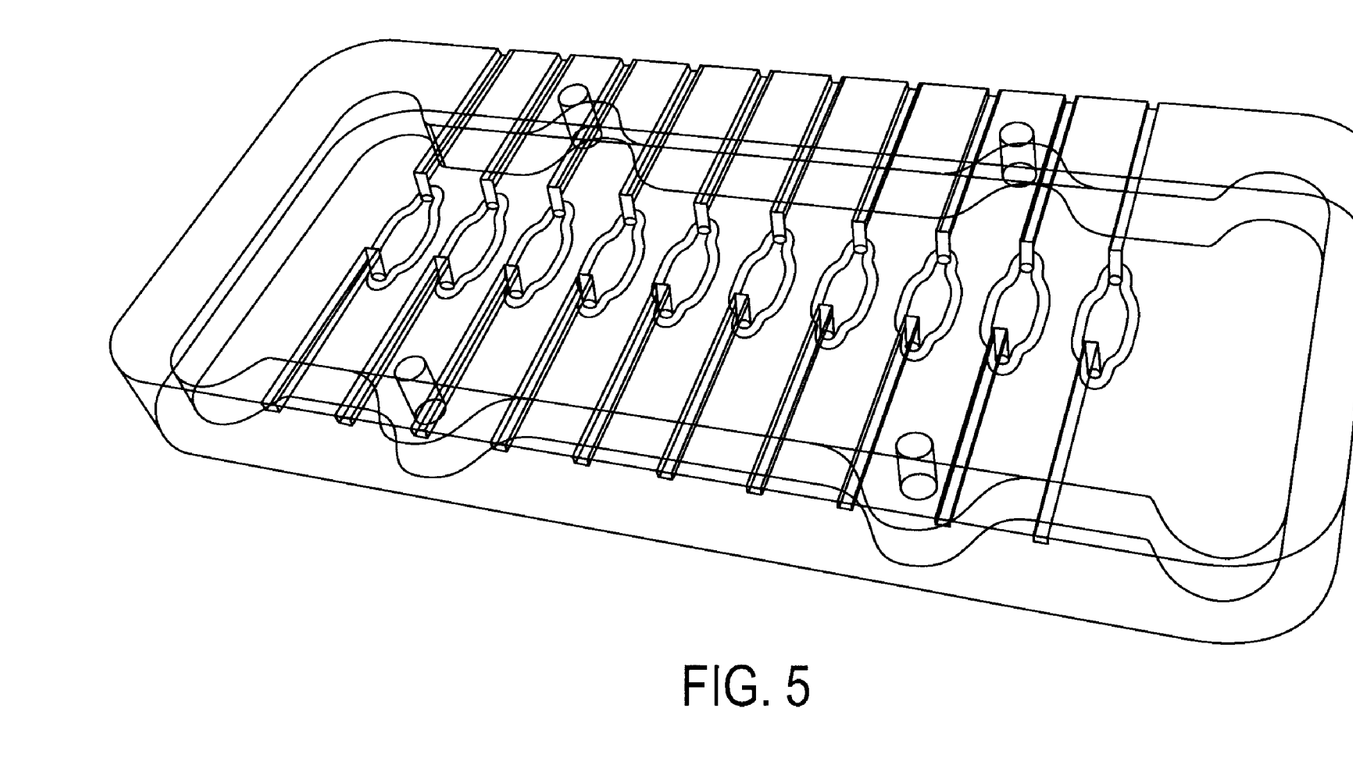
FIG. 5 is a multi-integrated fluid cell platform for parallel assay experiments.

The fifth embodiment, as depicted in FIG. 5, shows a multi-integrated fluid cell platform for parallel assay experiments performed under a microscope. As shown in the figure, it is simply a plurality of integrated fluid cells machined into a single plastic support body. Any of the previous embodiments could be followed to produce each of the integrated fluid cells for this device. Fluidic connections to the cells can be provided by microchannel extensions milled into the support body. A plastic cover plate can be secured over the microchannel extensions with doubled-sided acrylic adhesive tape to enclose the channels.

When present, the depth of the ridge in the support body can be about half the thickness of the gasket providing ample support to keep the gasket seated. In general, the ridge in the support body should be of sufficient depth to seat the gasket. The channel between the ridge and the mesa should optimally have a width that is slightly larger than the gasket width to allow room for expansion of the gasket as it is compressed.

Those skilled in the art would understand that the flow cell geometry is designed to encourage uniform laminar flow across the sample substrate.

The elastomer silicone gasket through which a water-tight seal is achieved is typically of the same shape as the channel is produced in a mold. The gasket forms the side walls of the fluid cell. The gaskets should be of sufficient height such that they make conformal contact between the free-standing mesa and the substrate. The gasket should be of sufficient height such that they can be slightly compressed and form a water-proof seal between the support body and substrate. Compression of the gasket occurs when the sample substrate and cartridge is pressed together.

Manufacturing of this invention can be accomplished using a CNC milling machine. The uniquely simple design of the integrated fluid cell makes other complicated and expensive manufacturing techniques such as micromachined silicon, embossed thermoplastic, injection molded plastic, or laser ablation unnecessary. The micromachining of glass or silicon is expensive and difficult to assemble, laser ablation too slow and limited to relatively small features, and both embossed and injection molded thermoplastics require an expensive master that is good for only one design.

A feature of this invention is that the cell design is independent of the support body. The cell design is restricted only by the surface area and location of the assay reaction on the planar substrate on which the fluid cell will be mounted over. In the case of an IC chip, other considerations may include the presence of wire bonds to the edge of the chip that the mesa must be designed to avoid. Therefore the basic design and manufacturing process is identical whether it is for a cartridge or a multi-cell platform for microscope observation.

The support body, planar substrate and elastomer silicone gasket are reusable in the embodiments which involve compression of a silicone layer to form the water-tight seal. The plastic body can be reused indefinitely for the life of the part. The elastomer silicone gasket will last for weeks. The elastomer silicone gasket, under compression, acts to both form a water-proof seal and define the integrated fluid cell inner wall boundaries. No adhesives are required for assembly. Silicone, such as poly(dimethylsiloxane) or PDMS, can be quickly cast (minutes) from a rapid prototyped mold. See, Duffy, et al., Rapid prototyping of microfluidic systems in poly(dimethylsiloxane). Anal. Chem. 70, 4974-4984.

The central surface of the mesa within the bounds of the elastomer silicone gasket can have added features machined into the surface that modify the characteristic laminar parabolic flow profile to, for example, one with a flatter leading edge. See Tamanaha, et al., Magnetic method for DNA detection on an arrayed solid state device, Micro Total Analysis Systems 2001, (Kluwer Academic Publishers. Boston. pp. 444-446) (2001). Such capabilities enable, for example, experimental enhancement of mass transfer conditions in biochemical analysis, or passive mechanisms for mixing in microfluidic channels.

The entire system is very versatile in accepting various planar substrates. If a microscope slide is used for the planar substrate, it can be held in place by a suitable base plate (acrylic if illuminating from below, aluminum if using coaxial illumination). If a sensor IC chip is to be used in a cartridge format, a properly mounted chip on a PCB carrier board can be held together by compression with screws or press-fit into the cartridge.

The system is compatible with all mechanisms of optical observation: fluorescence, luminescence, white light. etc. Fluidic connections to the integrated flow cells are amenable to tubes or microchannel extensions milled into the support body, see FIG. 7. The method is suited to manufacturing both recyclable and disposable devices.

The technology is fully expandable to a number of fields including small scale biochemical analysis, bioreactors, chemical, electrochemical, pharmacological and biological sensors.

It should be readily apparent to a person of ordinary skill in the art that although the motivation for this invention was to establish manufacturing methods within reach of the capabilities of a typical laboratory facility, there is no reason such methods could not be replaced by more sophisticated procedures such as LIGA and related MEMS manufacturing technology to produce systems with sub-millimeter dimensions in materials other than plastics (e.g. silicon, aluminum. etc.). Additionally, we have described a manufacturing method using CNC milling. If one wishes instead to mass produce cartridges, multi-cell platforms, etc., the devices can be injection molded using thermoplastics. Finally, a single inlet/outlet pair was described to pass fluid through the integrated cell. It is conceivable to add additional fluidic inlet/outlet ports to achieve hydrodynamic guidance of a sample stream within the cell.

What is claimed as new and desired to be protected by Letters Patent of the United States is:

1. A fluidic cell comprising
    a support body having a receiving surface for an assay substrate, a recessed area having a depth located within said receiving surface, a mesa located within said recessed area, wherein said mesa is configured to have a height that is less than the depth of said recessed area and at least two fluidic ports;
    an assay substrate in connection with said receiving surface; and
    a compressible layer located between said support body and said assay substrate, wherein said compressible layer is located around said mesa, wherein said compressible layer is configured to define the side walls of said fluidic cell and provide a seal around said mesa when said support body and said assay substrate are connected, wherein the difference between said depth of said recessed area and said height of said mesa is the height of said fluidic cell,
    wherein the mesa is integral with and of the same material as the support body, wherein said assay substrate is selected from sensor microchips, genomic arrays, or proteomic arrays.

2. The fluidic cell of claim 1 wherein said support body further comprises a raised ledge located around said compressible layer.

3. The fluidic cell of claim 1 wherein said compressible layer is comprised of an elastomer material.

4. The fluidic cell of claim 1 wherein said support body further comprises a raised ledge configured to align said assay substrate.

5. The fluidic cell as recited in claim 1 further comprising electrical connections to said assay substrate.

6. The fluidic cell of claim 1 wherein said support body is comprised of a transparent material.

7. The fluidic cell of claim 1 wherein said assay substrate is a carrier board having a sensor chip, wherein said carrier board is in connection with said support body.

8. The fluidic cell of claim 1 wherein said fluidic ports comprise a fluidic inlet port and a fluidic outlet port.

9. An array of fluidic cells comprising at least two fluidic cells of claim 1 located on the same support body.

* * * * *